United States Patent
Sandkamp et al.

(10) Patent No.: US 7,236,567 B2
(45) Date of Patent: Jun. 26, 2007

(54) METHOD AND APPARATUS FOR SYNCHRONIZING OPERATION OF AN X-RAY SYSTEM AND A MAGNETIC SYSTEM

(75) Inventors: Bernhard Sandkamp, Erlangen (DE); Ulrich Bill, Effeltrich (DE); Anton Nekovar, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/088,304

(22) Filed: Mar. 24, 2005

(65) Prior Publication Data

US 2006/0215816 A1 Sep. 28, 2006

(51) Int. Cl.
*H05G 1/56* (2006.01)
(52) U.S. Cl. .................. 378/114; 378/115; 600/407; 600/424
(58) Field of Classification Search ............ 378/114, 378/115, 116; 600/424, 407, 9, 10, 11
See application file for complete search history.

(56) References Cited

U.S. PATENT DOCUMENTS

| | | | |
|---|---|---|---|
| 4,953,554 A * | 9/1990 | Zerhouni et al. ............ 600/410 |
| 5,807,254 A * | 9/1998 | Meulenbrugge et al. ...... 378/63 |
| 6,031,888 A * | 2/2000 | Ivan et al. .................... 378/20 |
| 6,263,225 B1 * | 7/2001 | Howard, III ................ 600/378 |
| 6,330,303 B1 * | 12/2001 | Yamane et al. ............ 378/98.8 |
| 6,510,202 B2 * | 1/2003 | Tamura et al. .............. 378/155 |
| 6,973,162 B2 * | 12/2005 | Block et al. .................. 378/63 |
| 2005/0245817 A1 * | 11/2005 | Clayton et al. ............. 600/424 |
| 2005/0256398 A1 * | 11/2005 | Hastings et al. ............ 600/423 |

* cited by examiner

*Primary Examiner*—Edward J. Glick
*Assistant Examiner*—Chih-Cheng Glen Kao
(74) *Attorney, Agent, or Firm*—Schiff Hardin LLP

(57) ABSTRACT

An x-ray apparatus has a flat panel x-ray detector, the operation of which is susceptible to interference by strong magnetic fields. In order to allow the x-ray system to be operated concurrently with a magnetic system, such as a magnetic tracking system or a magnetic localization system, that emits a magnetic field of sufficient field strength to interfere with the operation of the flat panel x-ray detector, a control unit is provided that operates both the flat panel x-ray detector and the magnetic system. The control unit synchronizes operation of the magnetic system with the operation of the flat panel x-ray detector so that the magnetic system emits the magnetic field only at times that do not interfere with the operation of the flat panel x-ray detector.

13 Claims, 2 Drawing Sheets

METHOD AND APPARATUS FOR SYNCHRONIZING OPERATION OF AN X-RAY SYSTEM AND A MAGNETIC SYSTEM

BACKGROUND OF THE INVENTION

1. Field of the Invention

The present invention concerns a method and an apparatus for synchronizing the operation of an x-ray system and a magnetic system, and in particular concerns such a method and apparatus wherein the x-ray system has a flat panel x-ray detector.

2. Description of the Prior Art

Various types of medical procedures are conducted using magnetic tracking systems, wherein a magnetic field is generated externally of a patient and an object in the patient is tracked, or its location identified, by detecting and analyzing voltages induced at one or more coils carried by the object, that arise due to the changing magnetic field. Such magnetic tracking is used, for example, in PCI (percutaneous coronary intervention) and cardiac EP (electrophysiology) interventions and examinations. Such magnetic tracking systems are able to track a catheter or a stent in such procedures and examinations.

X-ray systems are also used in such procedures. Until recently, most x-ray systems employed an x-ray image intensifier for the purpose of detecting x-rays attenuated by the patient, coupled to a CCD camera for the purpose of producing video images from the detected x-rays. Such detection/imaging systems are not influenced by the magnetic fields generated by magnetic tracking systems, and therefore such x-ray systems were compatible for use with magnetic tracking systems. Another type of radiation detector is a flat panel x-ray detector. Such flat panel x-ray detectors were primarily used in cathlab C-arm systems, however, in recent years their use has become widespread for all types of x-ray systems used for medical interventional purposes, including virtually universal use in EP labs. The use of flat panel x-ray detectors has become so widespread that they are close to becoming the standard type of x-ray detector that is used for all medical x-ray systems.

Such flat panel x-ray detectors, however, are susceptible to magnetic fields of the type generated by a magnetic tracking system or other types of devices that produce a magnetic field, such as ablation systems. Such magnetic fields can produce image artifacts in the images generated by flat panel x-ray detectors.

SUMMARY OF THE INVENTION

An object of the present invention is to make an x-ray system employing a flat panel x-ray detector compatible for use with a magnetic system that produces a magnetic field capable of disturbing operation of the flat panel detector.

The above object is achieved in accordance with the present invention by a method and apparatus for synchronizing operation of an x-ray system, having a flat panel x-ray detector, and a magnetic system that produces a magnetic field that is capable of disturbing operation of the flat panel detector, wherein the magnetic system is activated only at times when the operation of the flat panel x-ray detector cannot be disturbed. For example, activation of the magnetic system may occur only at times when readout of image data from the flat panel detector is not taking place.

X-ray systems used for many medical applications, in particular cardiac applications, deliver a series of images. For each image, data must be read out from the flat panel x-ray detector. Typically, image series, with a frame rate of 30 Hz are obtained and displayed. Whenever generation of an image from the panel x-ray detector is desired, a so-called "frame request" signal is supplied to the control electronics of the flat panel detector. For an image series with a frame rate of 30 Hz, this means a frame request will be supplied to the flat panel detector at intervals of 33 ms. The frame request is followed by a period of time during which the x-ray source is enabled to emit x-rays, with the flat panel detector being sensitive during this time to detect x-ray radiation, which is integrated by the flat panel detector. When the active generation of x-rays stops, i.e. the x-ray source is no longer enabled, readout of the flat panel x-ray detector occurs. The inventive method and apparatus are based on the recognition that it is only during this readout period that the flat panel x-ray detector is susceptible to being influenced by the magnetic field generated by the magnetic system. Therefore, in accordance with the invention the magnetic system is operated in synchronization with the x-ray system so that the magnetic system is made active only during times other than the readout period. For example, the magnetic system can be activated during the same period that the x-ray source is enabled. Since the x-ray source is disenabled prior to readout of the flat panel x-ray detector, by substantially simultaneously deactivating the magnetic system, the magnetic system is not active during readout of data from the flat panel detector, and therefore the magnetic field associated with the operation of the magnetic system does not adversely affect this readout.

Examples of magnetic systems with which the invention can be used are magnetic tracking or localization systems, and ablation systems. As stated above, however, the invention is suitable for use with any type of device or system that produces a magnetic field that is capable of disturbing operation of the flat panel detector.

DESCRIPTION OF THE PREFERRED EMBODIMENTS

Figure 1:
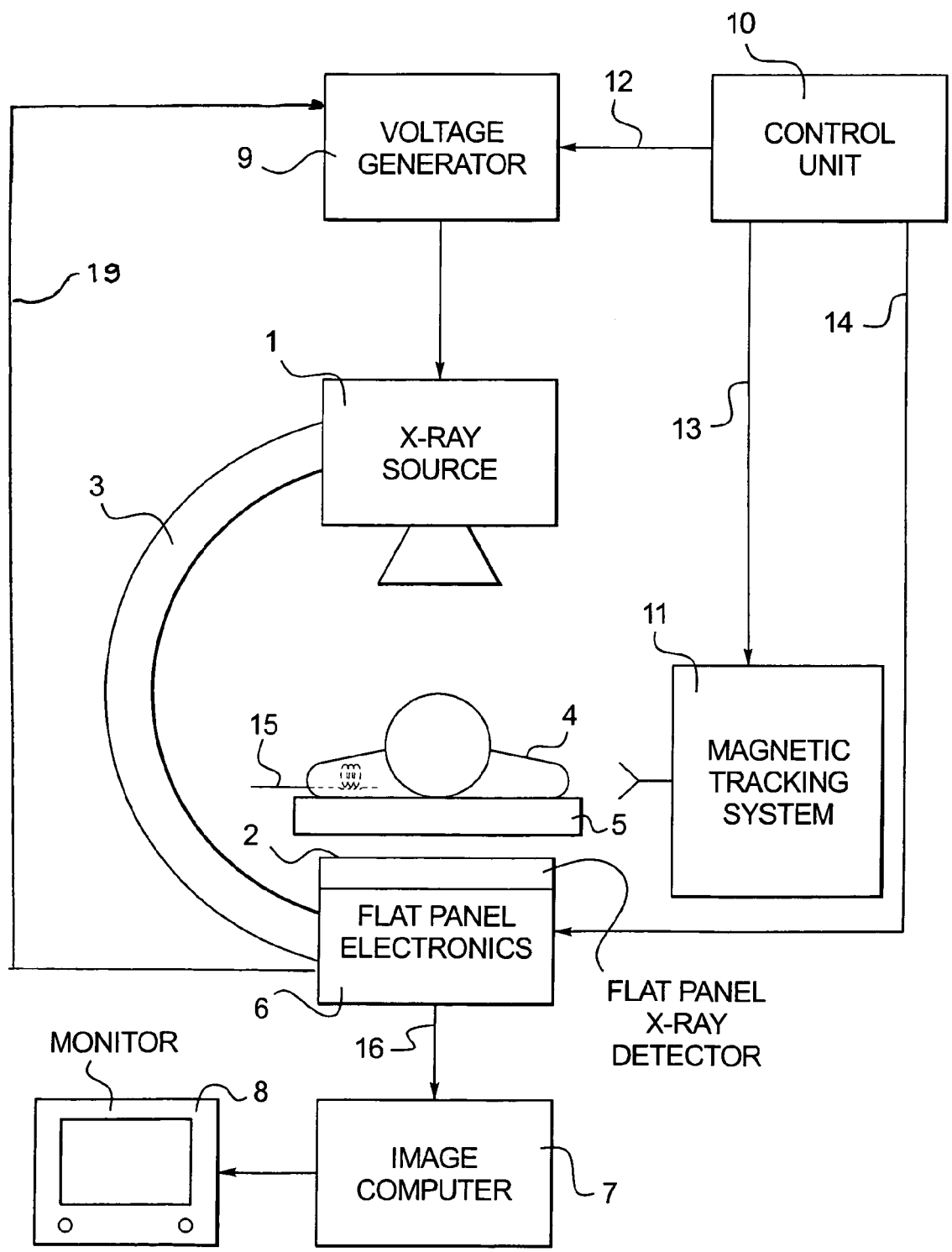
FIG. 1 is a schematic block diagram of an apparatus for synchronized operation of an x-ray system and a magnetic system, constructed and operating in accordance with the principles of the present invention.

The exemplary embodiment of the inventive apparatus shown in FIG. 1 includes an x-ray imaging system of the type commonly employed in cathlab procedures, although a catheter is not illustrated in FIG. 1 since it is not important for explaining the principles of the invention. The method and apparatus of the invention, however, are not limited to any particular type of x-ray system or type of intervention or examination undertaken with the x-ray system, but are applicable to any situation wherein an x-ray system, having a flat panel x-ray detector, is used in combination with a system that generates a magnetic field that is capable of disturbing operation of the flat panel x-ray detector.

In the embodiment shown in FIG. 1, an x-ray source 1 and a flat panel x-ray detector 2 are mounted on a C-arm 3, so that a patient 4, on a patient support 5 located between the x-ray source 1 and the flat panel x-ray detector 2, is irradiated with x-rays emitted by the x-ray source 1. X-rays attenuated by the patient 4 are detected by the flat panel x-ray detector 2.

Although support of the x-ray source 1 and the flat panel x-ray detector 2 on a C-arm 3 has been illustrated in the exemplary embodiment of FIG. 1, any type of supporting or mounting arrangement can be used, such as floor mounts, ceiling mounts, a gantry, etc.

The flat panel x-ray detector 2 has known flat panel electronics 6 associated therewith, which operate the flat panel x-ray detector 2, including effecting readout of image data therefrom. The image data read from the flat panel x-ray detector via the flat panel electronics 6 are supplied to an image computer via a line 16, which generates an image of the irradiated region of the examination subject 4 in a known manner, for display at a monitor 8. In some instances, the use of an image computer 7 may not be necessary, and video signals can be generated directly by the flat panel electronics 6.

The x-ray source 1 is supplied with the appropriate voltages and currents from a voltage generator 9 in a known manner. The voltage generator 9 is operated by a control unit 10.

The apparatus shown in FIG. 1 also includes a magnetic tracking system 11, as an example of a magnetic system that generates a magnetic field that is capable of disturbing operation of the flat panel x-ray detector 2. The magnetic tracking system 11 operates in a known manner to emit the aforementioned magnetic field. An object to be tracked by the magnetic tracking system 11, such as a catheter 15, carries a coil. As the catheter moves through the magnetic field generated by the magnetic tracking system 11, a voltage is induced across the coil by the changing magnetic field, thereby producing a current which is measured. For this purpose, leads or a wireless communication must be provided between the catheter 15 and the magnetic tracking system 11, but such items are known and are therefore omitted for clarity. By analyzing the currents in a known manner, the position and path of the catheter 15 are tracked. The magnetic tracking system 11 may have its own display medium, or may supply an output signal to a separate display, or to some other component that makes use of the tracking or localization information.

The control unit 10 controls the voltage generator 9 via a control line 12, which is standard. The control unit 10 also supplies a frame request signal to the flat panel detector electronics in a known manner via line 14. In accordance with the invention, an additional control line 13 the control unit 10 is provided that allow the control unit 10 to additionally control the magnetic tracking system 11. The control of the voltage generator 9, the magnetic tracking system 11 and the flat panel electronics 6 ensues in accordance with the invention in a synchronized manner, which is explained using the signals shown in FIG. 2 as examples.

Figure 2:
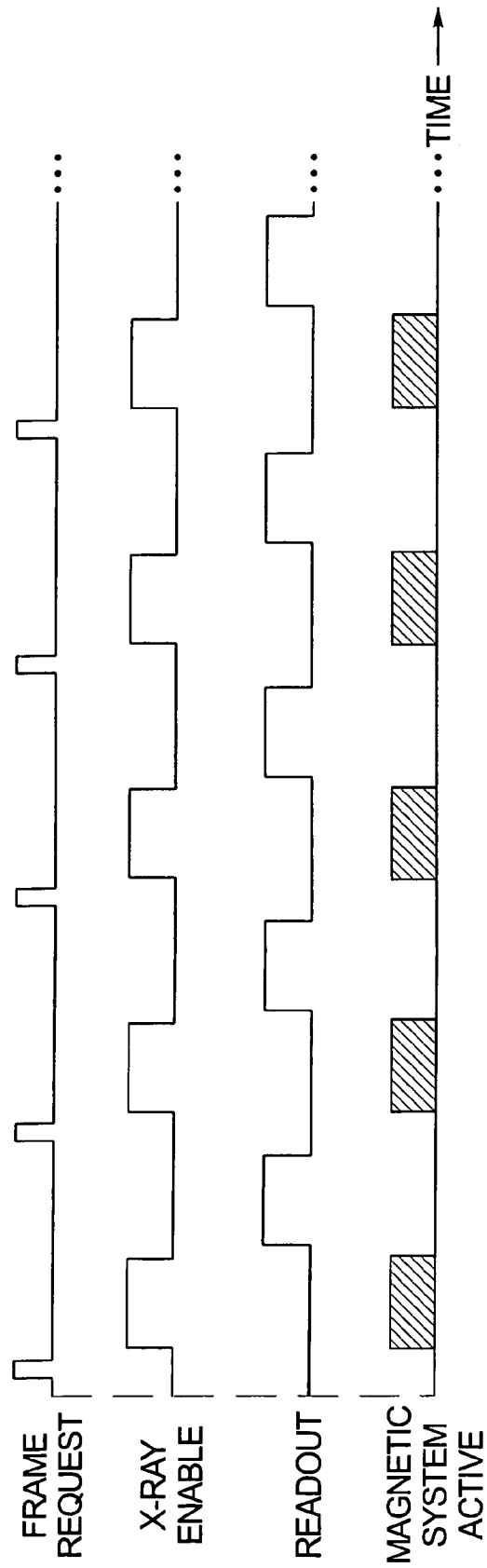
FIG. 2 shows the time relationship of different signals employed in the operation of the apparatus of FIG. 1, in accordance with the invention.

FIG. 2 shows, from top to bottom, a frame request signal, an x-ray enable signal, a readout signal, and a magnetic system activation signal. The signals are shown in respective horizontal axes indicating increasing time t.

When an image in an image series is intended to be generated, the control unit 10 emits the frame request signal via the control line 14 to the flat panel electronics 6. This prepares or activates the flat panel 2 to be sensitive for the detection of x-rays incident thereon. Substantially immediately thereafter, the flat panel electronics 6 supplies the x-ray enable signal via the line 19 to the voltage generator 9. The voltage generator 9, in turn, substantially for the duration of the x-ray enable signal, supplies appropriate operating voltages to the x-ray source 1 causing it to emit x-rays. The x-rays are attenuated by the patient 4 on the patient support 5, and are detected by the flat panel x-ray detector 2.

Substantially immediately after the end of the x-ray enable signal, the flat panel electronics 6 automatically reads out the data that have been integrated by the flat panel x-ray detector 2 during the time that the x-ray enable signal was present. Substantially immediately after the end of the readout of the flat panel x-ray detector 2, the control unit 10 generates another frame request signal or pulse, and the cycle is repeated.

As noted above, typically the pulses in the frame request signal will occur at a frame rate of 30 Hz, which means that the time interval between successive frame request pulses is 33 ms.

In accordance with the invention, the control unit synchronizes operation of the magnetic tracking system 11 with the aforementioned operation of the flat panel x-ray detector 2, by activating the magnetic tracking system 11 only at a time when operation of the flat panel detector 2 will not be disturbed by the magnetic field produced by the magnetic tracking system 11. For example, this can be only at a time when readout of the flat panel x-ray detector 2 is not occurring. This is accomplished by emitting a magnetic system activation signal from the control unit 10 via the control line 13 to the magnetic tracking system 11 when the flat panel detector 2 will not be disturbed, such as at a time other than the period occupied by the pulses in the readout signal. In the exemplary embodiment shown in FIG. 2, the activation of the magnetic tracking system 11 is shown to be substantially co-extensive with the emission of x-rays by the x-ray source 1, i.e., the pulse duration of the x-ray enable signal is substantially equal to the pulse duration of the magnetic system activation signal. It is not necessary, however, that the pulses of these two signals coincide or substantially coincide, nor is it even necessary that they overlap. It is only necessary that the activation pulse in the magnetic system activation signal not overlap with the pulses in the readout signal.

Figure 3:
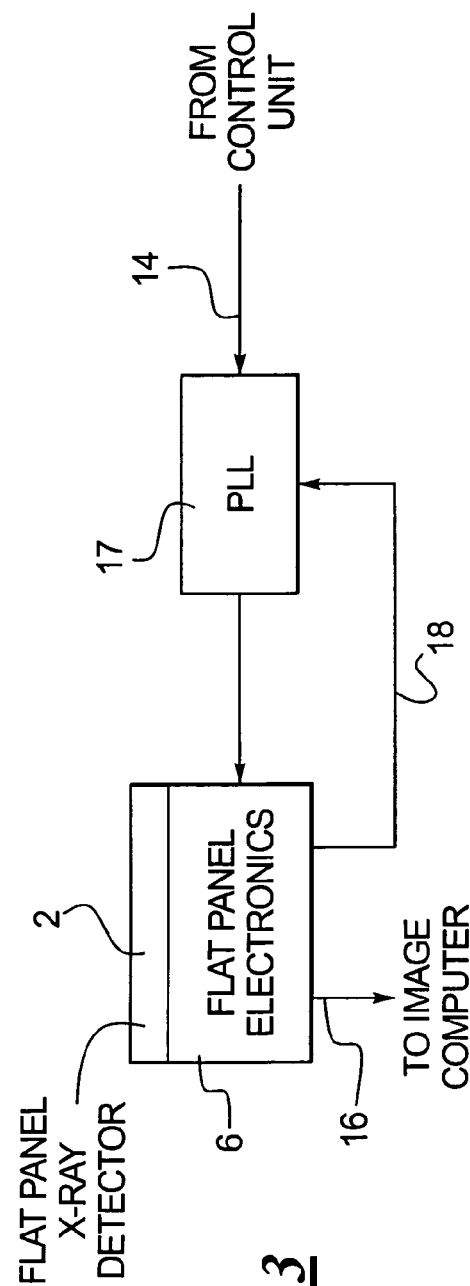
FIG. 3 is a block diagram of a portion of the apparatus of FIG. 1, illustrating a further embodiment.

A further embodiment schematically shown in FIG. 3 is applicable if the perturbations or disturbances in the operation of the flat panel x-ray detector 2 occur periodically at a frequency that is close to the frequency of the frame request signal. Under such circumstances, the disturbances can be detected in any suitable manner (such as by appropriate analysis by any known manner of the output of the flat panel x-ray detector 2) and a signal can be supplied to a phase locked loop (PLL) 17 via line 18 from the flat panel electronics 6. The phase locked loop 17 shifts the internal frame request signal so that the perturbations occur only during at time (phase) when the flat panel x-ray detector 2 will not be disturbed. In this embodiment, the control line 13 from the control unit 10 to the magnetic system is not needed.

The inventive method and apparatus therefore allow the magnetic tracking system 11 to be operated concurrently with the x-ray apparatus having the flat panel x-ray detector 2, without interference with the operation of the flat panel x-ray detector 2, and therefore without introducing image artifacts. Modern x-ray systems employing a flat panel x-ray detector therefore can be reliably used in environments where magnetic fields are generated by other components, such as cathlabs and EP labs. It is not necessary to restrict the x-ray imaging system used in such labs only to systems employing an x-ray image intensifier as the radiation detector.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray apparatus comprising:

an x-ray source;

a flat panel x-ray detector disposed to detect x-rays emitted by said x-ray source and operable in a cycle consisting of operation of said flat panel x-ray detector;

a magnetic system that emits a magnetic field in which said flat panel x-ray detector is disposed, said magnetic field having a field strength sufficient to disturb operation of said flat panel x-ray detector during a part of said cycle; and a control unit in communication with said flat panel x-ray detector and said magnetic system, said control unit activating said magnetic system to emit said magnetic field only at a time in said cycle other than during said part of said cycle.

2. An x-ray apparatus as claimed in claim 1 wherein said control unit supplies a signal to said flat panel x-ray detector to initiate said cycle.

3. An x-ray apparatus as claimed in claim 2 comprising a voltage generator connected to said x-ray source for supplying operating voltage to said x-ray source, and comprising flat panel x-ray detector electronics for electronically operating said x-ray flat panel detector in said cycle and in communication with said voltage generator to enable said voltage generator to supply said operating voltage to said x-ray source only outside of said part of said cycle.

4. An x-ray apparatus as claimed in claim 3 wherein said control unit activates said magnetic system substantially coextensively in time with enablement of said voltage generator.

5. An x-ray apparatus as claimed in claim 1 wherein said part of said cycle comprises a readout phase and wherein said control unit activates said magnetic system only within a time following initiation of said cycle and preceding said readout phase.

6. An x-ray apparatus as claimed in claim 1 wherein said magnetic system is a magnetic tracking system.

7. An x-ray apparatus as claimed in claim 1 wherein said magnetic system is an ablation system.

8. An x-ray apparatus as claimed in claim 1 comprising a C-arm on which said x-ray source and said flat panel x-ray detector are mounted.

9. A method for operating an x-ray apparatus having an x-ray source, a flat panel x-ray detector disposed to detect x-rays emitted by said x-ray source and operable in a cycle consisting of operation of said flat panel x-ray detector, and a magnetic system that emits a magnetic field in which said flat panel x-ray detector is disposed, said magnetic field having a field strength sufficient to disturb operation of said flat panel x-ray detector in a part of said cycle, and said method comprising the steps of:

placing a control unit in communication with said flat panel x-ray detector and said magnetic system; and via said control unit, initiating said cycle and activating said magnetic system to emit said magnetic field only at a time other than during said part of said cycle.

10. A method as claimed in claim 9 wherein said x-ray apparatus comprises a voltage generator connected to said x-ray source for supplying operating voltage to said x-ray source, and flat panel detector electronics for electronically operating said flat panel x-ray detector and wherein said method comprises placing said flat panel detector electronics in communication with said voltage generator and enabling said voltage generator via said flat panel detector electronics to supply said operating voltage to said x-ray source only outside of said part of said cycle.

11. A method as claimed in claim 10 comprising, via said control unit, activating said magnetic system substantially coextensively in time with enablement of said voltage generator.

12. A method as claimed in claim 9 wherein said part of said cycle comprises a readout phase, and wherein said method comprises, via said control unit, activating said magnetic system to emit said magnetic field only within a time following said initiation of said cycle and preceding said readout phase.

13. An x-ray apparatus comprising:

an x-ray source;

a flat panel x-ray detector disposed to detect x-rays emitted by said x-ray source;

flat panel x-ray detector electronics for electronically operating said flat panel x-ray detector in a cycle;

a control unit connected to said flat panel x-ray detector electronics for supplying a signal to said flat panel x-ray detector electronics to initiate said cycle, said signal having a frequency;

a magnetic system that emits a magnetic field in which said flat panel x-ray detector is disposed, said magnetic field having a field strength sufficient to disturb operation of said flat panel x-ray detector during a part of said cycle at a frequency approximating said frequency of said signal; and a phase locked loop connected between said flat panel x-ray detector electronics and said control unit for causing said signal from said control unit to be supplied to said flat panel x-ray detector electronics only at a time outside of said part of said cycle.

* * * * *